(12) United States Patent
Miura et al.

(10) Patent No.: US 9,965,914 B2
(45) Date of Patent: May 8, 2018

(54) MAGNETIC DETECTING DEVICE AND SHEET PROCESSING APPARATUS

(71) Applicant: Kabushiki Kaisha Toshiba, Minato-ku (JP)

(72) Inventors: Junji Miura, Naka-gun (JP); Seiji Ikari, Yokohama (JP); Tomonori Makino, Ota (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days. days.

(21) Appl. No.: 15/018,171

(22) Filed: Feb. 8, 2016

(65) Prior Publication Data
US 2016/0155282 A1    Jun. 2, 2016

Related U.S. Application Data

(63) Continuation of application No. PCT/JP2014/004144, filed on Aug. 8, 2014.

(30) Foreign Application Priority Data

Aug. 9, 2013  (JP) ................................ 2013-167049

(51) Int. Cl.
G07F 7/00   (2006.01)
G07D 7/04   (2016.01)
(Continued)

(52) U.S. Cl.
CPC ............... G07D 7/04 (2013.01); G01N 27/72 (2013.01); G01N 33/346 (2013.01);
(Continued)

(58) Field of Classification Search
CPC ...... G07D 7/04; G01N 27/72; B65H 2553/22; B65H 2553/822; B65H 2701/1714; B65H 2701/1912
See application file for complete search history.

(56) References Cited

U.S. PATENT DOCUMENTS 4,536,709 A * 8/1985 Ishida .................. H03K 17/954
                                                              194/206
4,864,238 A    9/1989 Seitz
(Continued)

FOREIGN PATENT DOCUMENTS

GB         1 202 534       8/1970
JP         4-58174         2/1992
(Continued)

OTHER PUBLICATIONS

International Search Report dated Nov. 18, 2014 in PCT/JP2014/004144, filed on Aug. 8, 2014, (2 pages).
(Continued)

Primary Examiner — Mark J Beauchaine
(74) Attorney, Agent, or Firm — Oblon, McClelland, Maier & Neustadt, L.L.P.

(57) ABSTRACT

A magnetic detecting device according to an embodiment includes: a magnetic sensor head in which a plurality of magnetic sensing elements including a first magnetic sensing element and a second magnetic sensing element are arranged; and an environmental magnetism corrector. The plurality of magnetic sensing elements is arranged in one line over a length that is greater than a width of a sheet, in a direction that is orthogonal to a movement direction of the sheet. The environmental magnetism corrector corrects a first output signal output by the first magnetic sensing element, based on a second output signal output by the second magnetic sensing element. The magnetic sensor head has a sheet passage area that faces a sheet that passes over the magnetic sensor head, the first magnetic sensing element is positioned inside the sheet passage area, and the second magnetic sensing element is positioned outside the sheet passage area.

11 Claims, 11 Drawing Sheets

(51) Int. Cl.
*G01R 33/09* (2006.01)
*G01R 33/00* (2006.01)
*G01R 33/10* (2006.01)
*G01N 33/34* (2006.01)
*G01N 27/72* (2006.01)

(52) U.S. Cl.
CPC ......... *G01R 33/0094* (2013.01); *G01R 33/09* (2013.01); *G01R 33/10* (2013.01)

(56) References Cited

U.S. PATENT DOCUMENTS

| | | | |
|---|---|---|---|
| 4,967,156 | A | 10/1990 | Seitz |
| 5,014,006 | A | 5/1991 | Seitz |
| 2001/0028246 | A1 | 10/2001 | Aruga et al. |
| 2004/0075427 | A1 | 4/2004 | Aruga et al. |
| 2008/0285839 | A1 | 11/2008 | Nakamura |
| 2015/0260805 | A1* | 9/2015 | Miura ................ G01R 33/1253 324/228 |
| 2017/0109956 | A1* | 4/2017 | Bartos ...................... G07D 7/04 |

FOREIGN PATENT DOCUMENTS

| | | |
|---|---|---|
| JP | 4-58174 A | 2/1992 |
| JP | 2585558 | 2/1997 |
| JP | 2000-346920 | 12/2000 |
| JP | 2000-346920 A | 12/2000 |
| JP | 2001-266205 | 9/2001 |
| JP | 2002-98744 | 4/2002 |
| JP | 2002-98744 A | 4/2002 |
| JP | 2005-257440 | 9/2005 |
| JP | 2005-257440 A | 9/2005 |
| JP | 2009-121872 | 6/2009 |
| JP | 2009-169712 | 7/2009 |
| JP | 2012-43361 | 3/2012 |
| JP | 2013-120538 | 6/2013 |

OTHER PUBLICATIONS

Extended European Search Report dated Aug. 4, 2016 in Patent Application No. 14834024.3, (13 pages).
Japanese Office Action dated Sep. 12, 2017 in Patent Application No. 2013-167049, (3 pages).

* cited by examiner

MAGNETIC SENSOR SIGNAL BEFORE PROCESSING

MAGNETIC SENSOR SIGNAL AFTER MOVING AVERAGE PROCESSING

MAGNETIC DETECTING DEVICE AND SHEET PROCESSING APPARATUS

CROSS-REFERENCE TO RELATED APPLICATION

This application is based upon and claims the benefit of priority from Japanese Patent Application No. 2013-167049, filed on Aug. 9, 2013; the entire contents of which are incorporated herein by reference. This application is a continuation application of International Application No. PCT/JP2014/004144 filed on Aug. 8, 2014.

TECHNICAL FIELD

Embodiments of the present invention relate to a magnetic detecting device and a sheet processing apparatus.

BACKGROUND ART

Currently, sheets such as bills are printed in many countries in the world. As one of techniques for preventing counterfeiting of securities such as bills, there is a printing technique using a magnetic ink.

Also, there is a technique for reading magnetic properties of securities printed using the printing technique using a magnetic ink.

Magnetic detecting devices for reading magnetic properties of sheets such as securities detect magnetic properties of the sheets, in a state of being installed in various apparatuses. For example, the magnetic detecting devices are installed in sheet processing apparatuses for determining the authenticity of bills, and detect magnetic properties of the bills.

In sheet processing apparatuses, for example, a large number of electrical devices such as an alternating-current motor used to generate rotational power or circulate air and a power supply transformer used to generate a direct-current voltage from an alternating-current voltage are arranged.

These electrical devices discharge magnetic noise out of the electrical devices based on the operation principles.

Accordingly, magnetic sensing units in magnetic detecting devices installed in the sheet processing apparatus may detect a surrounding environmental magnetic field such as magnetism generated by the electrical devices, as well as detecting magnetic properties of sheets. In this case, the magnetic detecting devices cannot precisely detect magnetic properties of sheets.

DESCRIPTION OF EMBODIMENTS

In order to achieve the above-described object, a magnetic detecting device according to an embodiment includes: a magnetic sensor head in which a plurality of magnetic sensing elements including a first magnetic sensing element and a second magnetic sensing element are arranged; and an environmental magnetism corrector. The plurality of magnetic sensing elements is arranged in one line over a length that is greater than a width of a sheet, in a direction that is orthogonal to a movement direction of the sheet. The environmental magnetism corrector corrects a first output signal output by the first magnetic sensing element, based on a second output signal output by the second magnetic sensing element. The magnetic sensor head has a sheet passage area that faces a sheet that passes over the magnetic sensor head, the first magnetic sensing element is positioned inside the sheet passage area, and the second magnetic sensing element is positioned outside the sheet passage area.

Hereinafter, embodiments will be described.

EMBODIMENTS

First Embodiment

Figure 1:
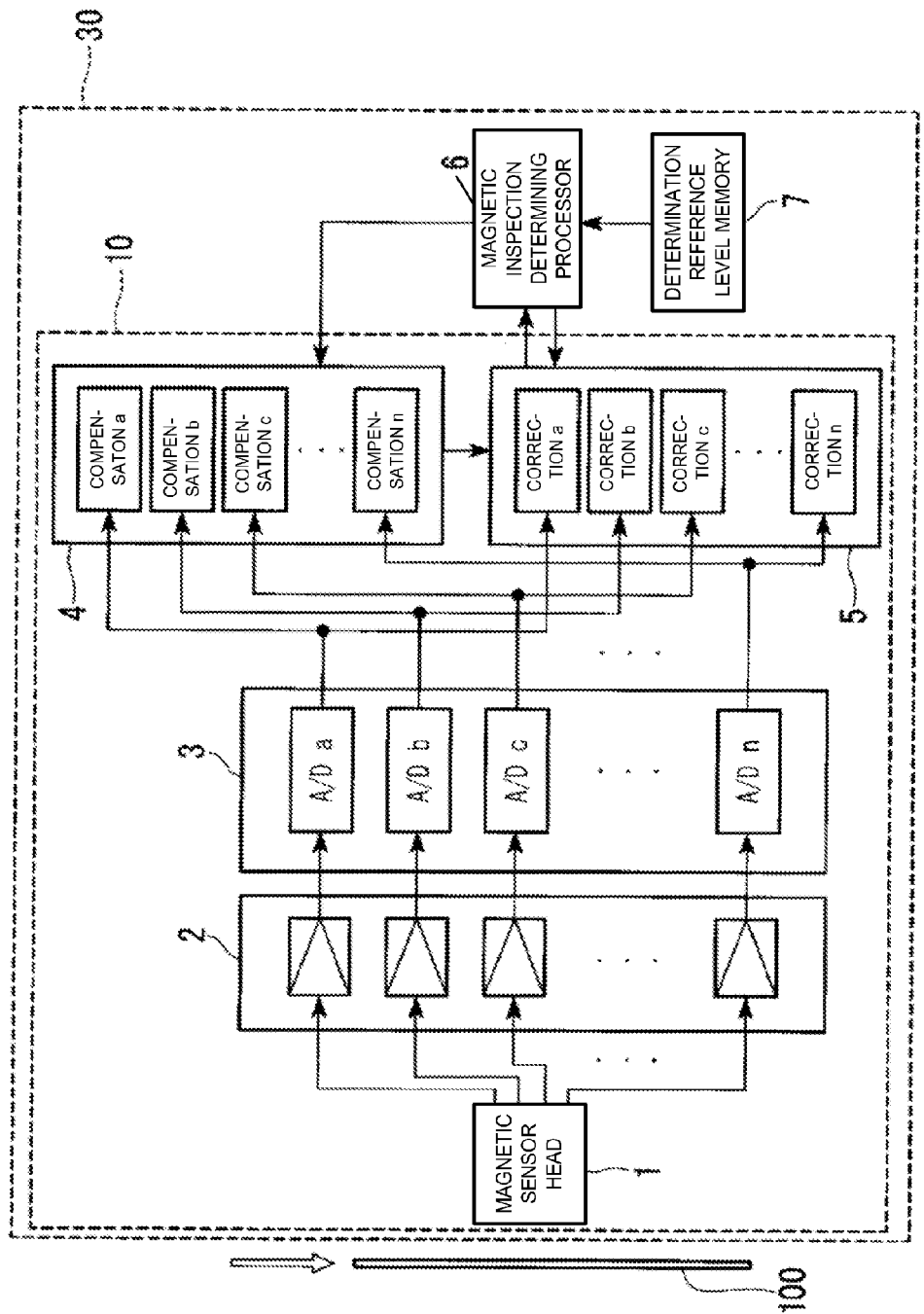
FIG. 1 is a diagram showing the configuration of an authenticity determining apparatus including a magnetic detecting device according to a first embodiment.

FIG. 1 is a diagram showing the configuration of an authenticity determining apparatus 30 including a magnetic detecting device 10 according to the first embodiment.

As shown in FIG. 1, the magnetic detecting device 10 according to the first embodiment includes a magnetic sensor head 1, a signal amplifier circuit 2, an A/D converter circuit 3, a compensation signal generator 4, and an environmental magnetism corrector 5. Furthermore, the authenticity determining apparatus 30 includes a magnetic detecting device 10, a magnetic inspection determining processor 6, and a determination reference level memory 7.

Figure 2:
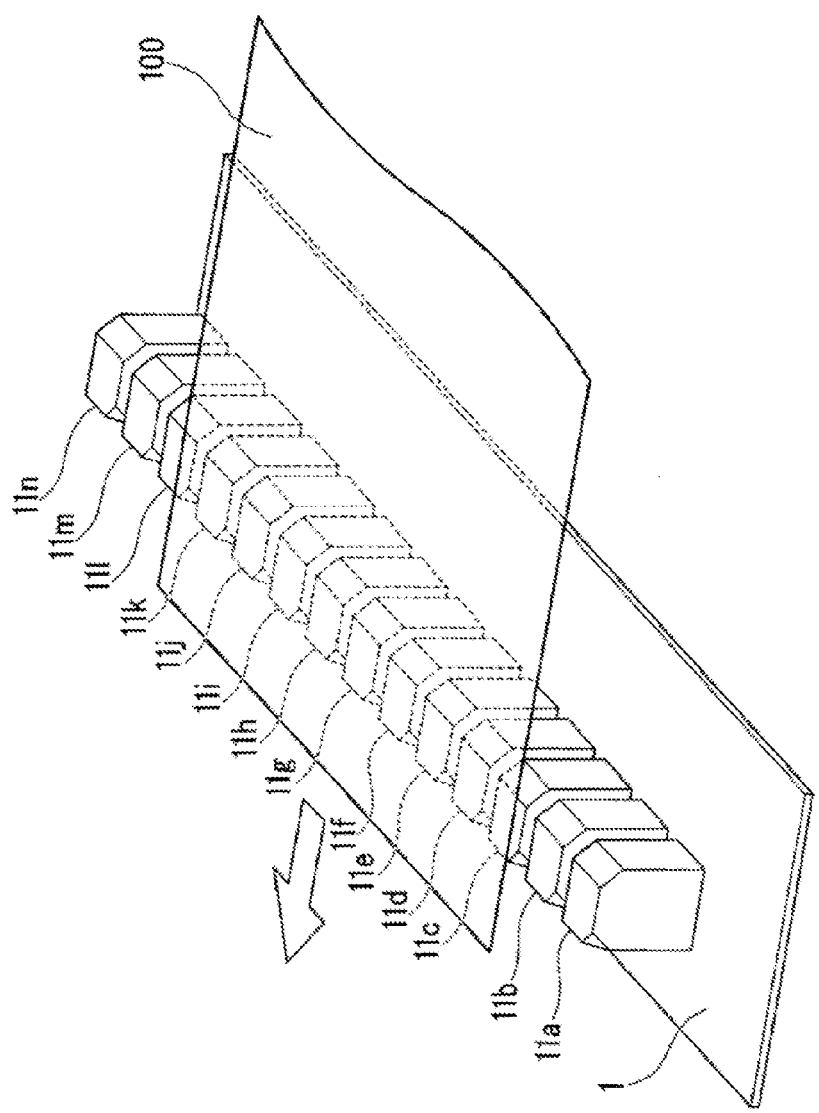
FIG. 2 is a view showing an example of a magnetic sensor head of the magnetic detecting device according to the first embodiment.

As shown in FIG. 2, the magnetic sensor head 1 of the magnetic detecting device 10 has a plurality of magnetic sensing elements 11 (11a, 11b, 11c, . . . ) arranged in one line over a length that is greater than a width of a sheet 100, in a direction that is orthogonal to a movement direction of the sheet 100. The sheet 100 whose magnetic properties are to be detected passes over the magnetic sensor head 1. In the magnetic sensor head 1, a sheet passage area is an area that faces the sheet 100, and is an area over which the sheet 100 from one edge to the other edge thereof, in the direction that is orthogonal to the movement direction of the sheet 100, passes. The magnetic sensing elements 11 positioned inside the sheet passage area are functional units for detecting magnetic properties of the sheet 100. Furthermore, the magnetic sensing elements 11 positioned outside the sheet passage area are functional units for detecting magnetic noise depending on the surrounding environment. The magnetic sensor head 1 is a functional unit for outputting analog signals according to the magnetic properties detected by these magnetic sensing elements 11. Note that the magnetic sensing elements 11a, 11b, 11c, . . . respectively have magnetic sensing faces that are formed on the same plane and along one straight line, and are collectively referred to as "magnetic sensing elements 11".

The signal amplifier circuit 2 is a functional unit for amplifying the analog signals output by the magnetic sensing elements 11 of the magnetic sensor head 1, and outputting the amplified analog signals.

The A/D converter circuit 3 is a functional unit for converting the amplified analog signals output by the signal amplifier circuit 2 into digital signals, and outputting the digital signals.

The compensation signal generator 4 is a functional unit for performing processing that removes a sudden change with respect to the time axis direction, from the digital signals output by the A/D converter circuit 3. Furthermore, the compensation signal generator 4 is a functional unit for specifying digital signals corresponding to the analog signals output by the magnetic sensing elements 11 positioned outside the sheet passage area, based on sheet passage position information and the like from a processor for optically detecting a sheet passage position, and outputting the specified digital signals to the environmental magnetism corrector 5.

The environmental magnetism corrector 5 is a functional unit for specifying digital signals corresponding to the analog signals output by the magnetic sensing elements 11 positioned inside the sheet passage area, based on sheet passage position information and the like from the processor for optically detecting a sheet passage position. Furthermore, the environmental magnetism corrector 5 is a functional unit for correcting the digital signals specified by the environmental magnetism corrector 5, based on the digital signals input from the compensation signal generator 4.

The magnetic inspection determining processor 6 is a functional unit for determining the authenticity of the sheet 100, based on the corrected digital signals output by the environmental magnetism corrector 5 and determination parameters stored in the determination reference level memory 7.

The determination reference level memory 7 is, for example, a memory for storing various types of data necessary for device operations in the magnetic detecting device 10, such as preset parameters for determining the authenticity of the sheet 100.

FIG. 2 is a view showing an example of the magnetic sensor head 1 of the magnetic detecting device 10 according to the first embodiment. As described above, the magnetic sensor head 1 has the plurality of magnetic sensing elements 11. For example, the magnetic sensor head 1 in this drawing includes 14 magnetic sensing elements consisting of magnetic sensing elements 11a to 11n.

The magnetic sensing elements 11 positioned inside the sheet passage area are the magnetic sensing elements 11c to 11k. The magnetic sensing elements 11 positioned inside the sheet passage area are hereinafter referred to as first magnetic sensing elements 111, which are first magnetism detecting units. Furthermore, magnetism detection results detected by the first magnetic sensing elements 111 are referred to as first magnetism detection results.

The magnetic sensing elements 11 positioned outside the sheet passage area are the magnetic sensing elements 11a, 11b, 11l, 11m, and 11n. The magnetic sensing elements 11 positioned outside the sheet passage area are hereinafter referred to as second magnetic sensing elements 112, which are second magnetism detecting units. Furthermore, magnetism detection results detected by the second magnetic sensing elements 112 are referred to as second magnetism detection results.

The magnetic sensing elements 11 that will function as the first magnetic sensing elements 111 and the magnetic sensing elements 11 that will function as the second magnetic sensing elements 112 change in accordance with the size of the sheet 100, the passage position of the sheet 100, and the number and arrangement of magnetic sensing elements 11, and are determined, for example, based on sheet passage position information and the like from the processor for optically detecting a sheet passage position.

Figure 3:
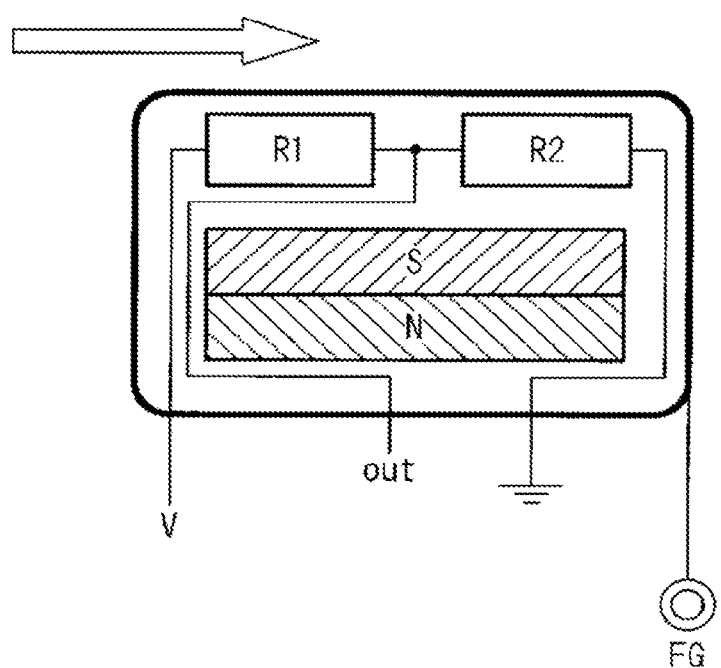
FIG. 3 is a diagram showing an example of a magnetic sensing element included in the magnetic sensor head of the magnetic detecting device according to the first embodiment.

FIG. 3 is a diagram showing an example of the magnetic sensing element 11 included in the magnetic sensor head 1 of the magnetic detecting device 10 according to the first embodiment. The magnetic sensing element 11 includes, for example, semiconductor magneto-resistive elements (SMRE). As shown in this drawing, the magnetic sensing element 11 has two magneto-resistive elements R1 and R2 made of indium antimonide single crystal (InSb) semiconductor or the like, and a permanent magnet disposed near the rear faces of the magneto-resistive elements R1 and R2. In the magnetic sensing element 11, when a magnetic substance moves parallel to the magneto-resistive elements in a bias magnetic field formed by the permanent magnet, magnetic field lines of the permanent magnet change, so that the resistance values of the magneto-resistive elements change. In the magnetic sensing element 11, a difference between the resistance values of the two magneto-resistive elements R1 and R2 is obtained as an electrical signal. In this example, the two magneto-resistive elements R1 and R2 are arranged along the movement direction of the sheet 100.

Note that the magnetic sensing element 11 may have, for example, thin alloy films mainly made of ferromagnetic metal such as nickel (Ni), iron (Fe), or the like, as the magneto-resistive elements R1 and R2.

Figure 4:
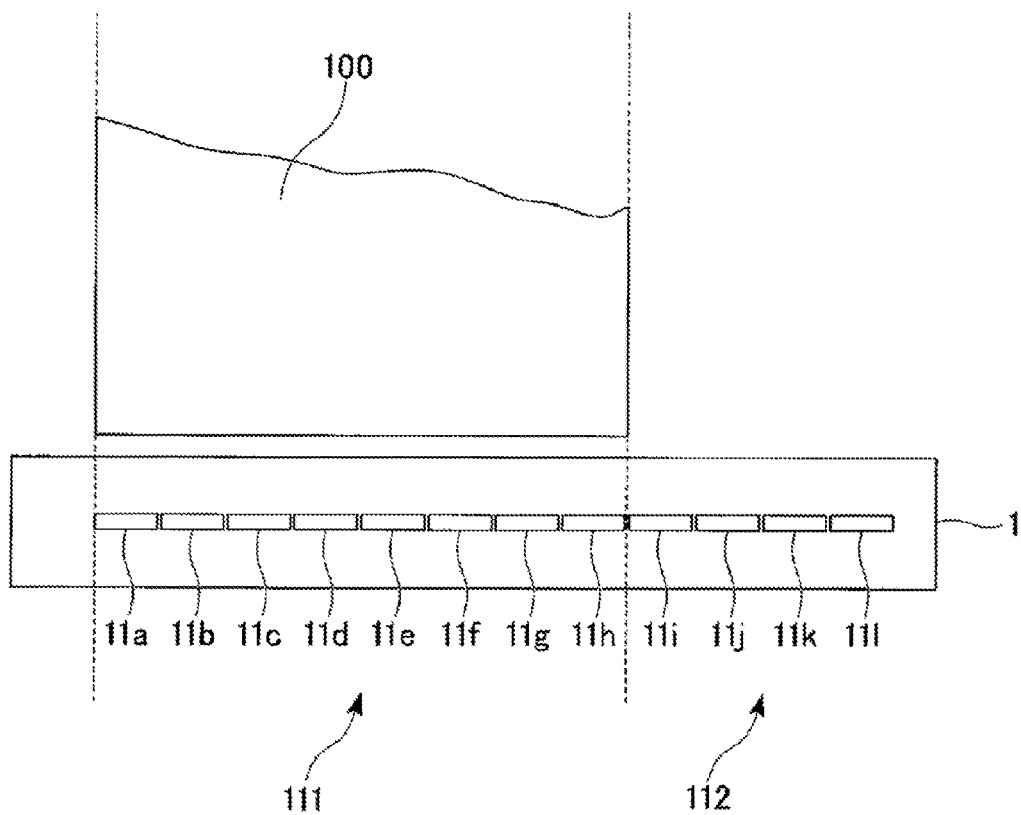
FIG. 4 is a view showing an arrangement example of magnetic sensing elements in the magnetic sensor head of the magnetic detecting device according to the first embodiment.
Figure 5:
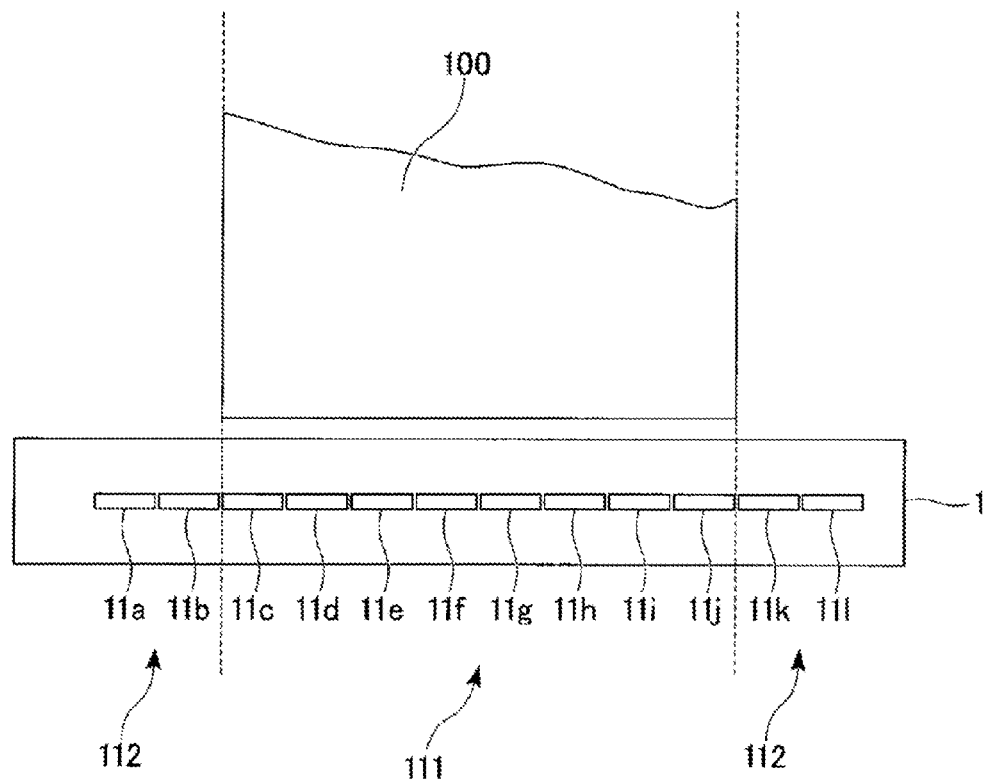
FIG. 5 is a view showing another arrangement example of the magnetic sensing elements in the magnetic sensor head of the magnetic detecting device according to the first embodiment.
Figure 6:
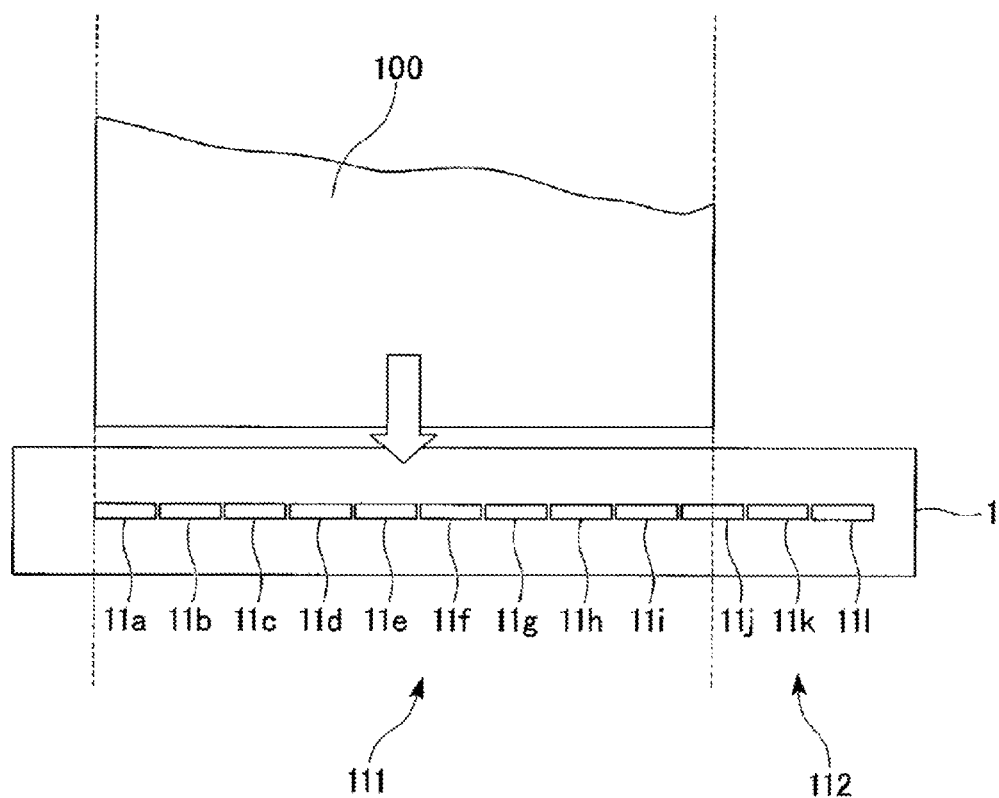
FIG. 6 is a view showing another arrangement example of the magnetic sensing elements in the magnetic sensor head of the magnetic detecting device according to the first embodiment.
Figure 7:
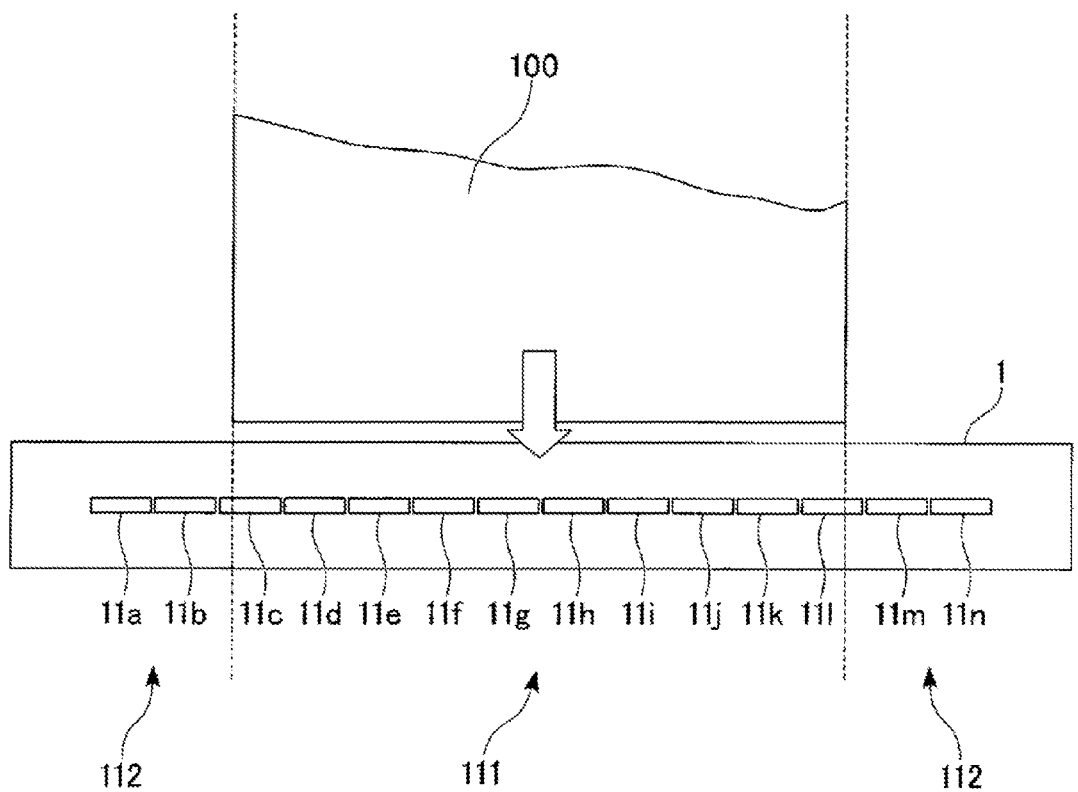
FIG. 7 is a view showing another arrangement example of the magnetic sensing elements in the magnetic sensor head of the magnetic detecting device according to the first embodiment.

FIG. 4 is a view showing an arrangement example of the magnetic sensing elements 11 in the magnetic sensor head 1 of the magnetic detecting device 10 according to the first embodiment. FIG. 5 is a view showing another arrangement example of the magnetic sensing elements 11 in the magnetic sensor head 1 of the magnetic detecting device 10 according to the first embodiment. FIG. 6 is a view showing another arrangement example of the magnetic sensing elements 11 in the magnetic sensor head 1 of the magnetic detecting device 10 according to the first embodiment. FIG. 7 is a view showing another arrangement example of the magnetic sensing elements 11 in the magnetic sensor head 1 of the magnetic detecting device 10 according to the first embodiment.

As shown in FIGS. 4 to 7, there are various types of the magnetic sensor head 1 that are classified according to the position of the sheet passage area and the number of magnetic sensing elements 11. The magnetic sensor head 1 includes the plurality of magnetic sensing elements 11. The magnetic sensing elements 11 are arranged in one line along a direction that is orthogonal to the movement direction of the sheet 100. The magnetic sensing faces of the magnetic sensing elements 11 arranged in one line are arranged so as to be capable of detecting magnetic properties of the entire area of the sheet 100. Furthermore, the magnetic sensing faces of the magnetic sensing elements 11 arranged in one line are arranged outside the sheet passage area as well so as to be capable of detecting magnetic properties outside the sheet passage area.

In this manner, in the magnetic sensor head 1, the magnetic sensing elements 11 respectively having magnetic sensing areas are arranged in one line, and the magnetic sensing elements 11 are arranged in a similar manner both inside and outside the sheet passage area. That is to say, in the magnetic sensor head 1, the magnetic sensing elements 11 for detecting magnetic properties of the sheet 100 when the sheet 100 passes over the magnetic sensor head 1 and the magnetic sensing elements 11 for detecting magnetic noise depending on the surrounding environment when the sheet 100 passes over the magnetic sensor head 1 are arranged in one line.

Ideally, at least one second magnetic sensing element 112 for detecting magnetic noise depending on the surrounding environment is disposed on the outer side of the first magnetic sensing elements 111 positioned inside the sheet passage area.

For example, FIG. 4 shows a case in which the sheet 100 passes over the area of eight magnetic sensing elements 11a to 11h among 12 magnetic sensing elements 11 of the magnetic sensor head 1. In this case, the magnetic sensing elements 11a to 11h function as the first magnetic sensing elements 111. The magnetic sensing elements 11i to 11l function as the second magnetic sensing elements 112.

FIG. 5 shows a case in which the sheet 100 passes over the area of eight magnetic sensing elements 11c to 11j among 12 magnetic sensing elements of the magnetic sensor head 1. In this case, the magnetic sensing elements 11c to 11j function as the first magnetic sensing elements 111. The magnetic sensing elements 11a, 11b, 11k, and 11l function as the second magnetic sensing elements 112.

FIG. 6 shows a case in which the sheet 100 passes over the area of 10 magnetic sensing elements 11a to 11j among 12 magnetic sensing elements of the magnetic sensor head 1. In this case, the magnetic sensing elements 11a to 11j function as the first magnetic sensing elements 111. The magnetic sensing elements 11k and 11l function as the second magnetic sensing elements 112.

FIG. 7 shows a case in which the sheet 100 passes over the area of 10 magnetic sensing elements 11c to 11l among 14 magnetic sensing elements of the magnetic sensor head 1. In this case, the magnetic sensing elements 11c to 11l function as the first magnetic sensing elements 111. The magnetic sensing elements 11a, 11b, 11m, and 11n function as the second magnetic sensing elements 112.

If the number of types of the sheets 100 is one or if the passage positions of the sheets 100 can be controlled, the sheet passage area of the magnetic sensor head 1 is substantially unchanged. Accordingly, the magnetic sensing element(s) 11 only for detecting magnetic noise may be disposed outside the sheet passage area. On the other hand, if a plurality of types of the sheets 100 are used in a mixed manner or if the sheet passage positions over the magnetic sensor head 1 vary even in the case where the number of types of the sheets 100 is one, the first magnetic sensing elements 111 and the second magnetic sensing elements 112 may be determined by detecting the sheet passage positions using other detection means or sensors (not shown). For example, sheet passage position information may be obtained from the processor for optically detecting a sheet passage position, and, based on that information, the inside and the outside of the sheet passage area in the magnetic sensor head 1 may be determined. Furthermore, proximity sensors for detecting whether or not the sheet 100 is present are provided immediately before the magnetic sensor head 1. The inside and the outside of the sheet passage area in the magnetic sensor head 1 may be determined based on whether or not the sheet 100 is present detected by the proximity sensors.

Figure 8A:
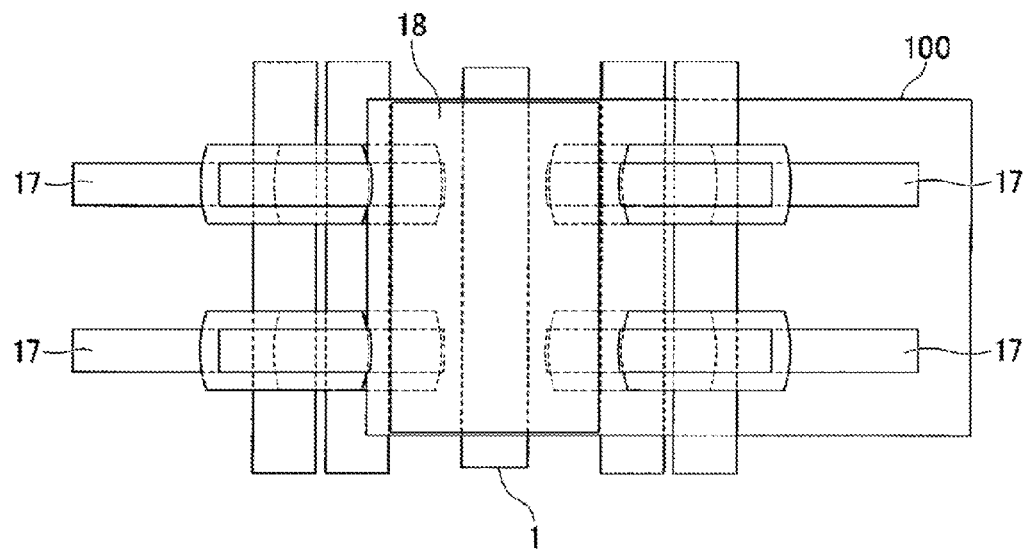
FIG. 8A is a view showing an example of a conveying structure around the magnetic sensor head of the magnetic detecting device according to the first embodiment.
Figure 8B:
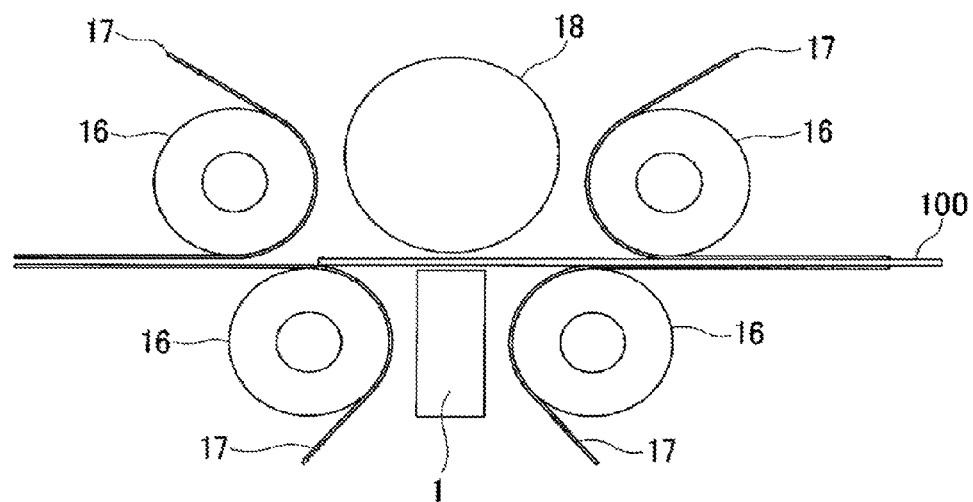
FIG. 8B is a view showing an example of the conveying structure around the magnetic sensor head of the magnetic detecting device according to the first embodiment.

FIG. 8A is a view showing an example of a conveying structure around the magnetic sensor head 1 of the magnetic detecting device 10 according to the first embodiment when viewed from above. FIG. 8B is a view showing an example of the conveying structure around the magnetic sensor head 1 of the magnetic detecting device 10 according to the first embodiment when viewed from the front.

As shown in FIGS. 8A and 8B, the magnetic detecting device 10 according to the first embodiment includes conveying rollers 16, conveying belts 17, and a conveying assist roller 18, around the magnetic sensor head 1.

In the magnetic detecting device 10 according to the first embodiment, the sheet 100 such as a bill that has been moved from the upstream side to the downstream side in the conveying direction in a state of being held between the conveying belts 17 is released, magnetic print information on the sheet 100 is read by the magnetic sensor head 1, and the sheet 100 is again held between the conveying belts 17 and is moved thereby.

In FIG. 8B, the conveying assist roller 18 is disposed in order to assist the conveyance when a sheet passes over the magnetic sensing faces of the magnetic sensing elements 11 in the magnetic sensor head 1. The conveying assist roller 18 has a function of causing the sheet 100 released from the conveying belts 17 to be held between the conveying belts 17 on the opposite side without being stopped. At the same time, the conveying assist roller 18 has a function of restricting the passage position of the sheet 100 over the magnetic sensing faces of the magnetic sensing elements 11 in the magnetic sensor head 1. Furthermore, the conveying assist roller 18 has a function of conveying the sheet 100 without stopping the sheet 100, while maintaining the distance between the magnetic sensor head 1 and the sheet 100, that is, the detected gap, within a predetermined range.

The conveying assist roller 18 is made of a non-magnetic material. The conveying assist roller 18 rotates at an outer circumferential speed similar to the belt conveying speed of the conveying belts 17, thereby generating an auxiliary power for moving the sheet 100.

Hereinafter, an example of processing performed by the authenticity determining apparatus 30 including the magnetic detecting device 10 according to the first embodiment will be described. In the example described below, an inspection device disposed on the upstream side optically detects a sheet passage position, and the first magnetic sensing elements 111 and the second magnetic sensing elements 112 are determined based on the sheet passage position information received from the inspection device.

First, a user sets the sheet 100 at a predetermined position. Then, the inspection device disposed upstream of the magnetic detecting device 10 performs inspection and processing on the sheet 100 as shown in a third embodiment, which will be described later. The inspection device disposed upstream of the magnetic detecting device 10 sends out the sheet 100 to the magnetic detecting device 10.

When the sheet 100 is sent from the inspection device into the magnetic detecting device 10, the conveying belts 17 of the magnetic detecting device 10 hold the sheet 100 therebetween. Then, for example, as described in FIG. 8B, the conveying belts 17 release the sheet 100 that has been held therebetween, and convey the sheet 100 via the conveying assist roller 18 to the conveying belts 17 on the opposite side without stopping the sheet 100.

During the conveyance, the magnetic sensing elements 11 of the magnetic sensor head 1 detect magnetic properties when the sheet 100 passes over the magnetic sensor head 1. The magnetic sensor head 1 output analog signals corresponding to the magnetic properties respectively detected by the magnetic sensing elements 11, to the signal amplifier circuit 2.

When the signal amplifier circuit 2 receives input of the analog signals from the magnetic sensor head 1, amplifiers of the signal amplifier circuit 2 respectively amplify the input analog signals so as to obtain a signal amplitude necessary for the processing by the A/D converter circuit 3 that is located after the signal amplifier circuit 2. Then, the signal amplifier circuit 2 outputs the amplified analog signals to the A/D converter circuit 3.

Upon receiving input of the amplified analog signals from the signal amplifier circuit 2, the A/D converter circuit 3 samples each of the input analog signals at a predetermined timing. Then, for example, the A/D converter circuit 3 compares a sampled signal with a reference signal, and converts the sampled signal into a digital signal. The A/D converter circuit 3 outputs each converted digital signal to the compensation signal generator 4 and the environmental magnetism corrector 5. Note that the A/D converter circuit 3 may be any circuit that can convert analog signals into digital signals at a necessary level of precision, and there is no limitation on its circuit system.

The compensation signal generator 4 receives input of the digital signals of the magnetic properties from the A/D converter circuit 3. The compensation signal generator 4 performs "moving average" processing or "smoothing" processing for averaging signals in a plurality of samples with respect to a time axis direction, on each of the input digital signals of the magnetic properties, thereby performing processing equivalent to low-pass filtering for reducing sudden changes in signals with respect to the time. Furthermore, the compensation signal generator 4 calculates "average values" of the digital signals subjected to the processing equivalent to low-pass filtering, and stores them in a memory.

Furthermore, the environmental magnetism corrector 5 receives input of the digital signals of the magnetic properties from the A/D converter circuit 3. The environmental magnetism corrector 5 stores the input digital signals of the magnetic properties, in a memory.

The inspection device disposed upstream of the magnetic detecting device 10 transmits passage position information, which is a result obtained by optically detecting the passage position of the sheet 100, to the compensation signal generator 4 and the environmental magnetism corrector 5 at a predetermined timing.

Upon receiving the passage position information from the inspection device, the compensation signal generator 4 specifies an area over which each sheet 100 passes in the magnetic sensor head 1, based on the passage position information. That is to say, the compensation signal generator 4 specifies the sheet passage area of the magnetic sensor head 1. Then, the compensation signal generator 4 specifies the second magnetic sensing elements 112 positioned outside the specified sheet passage area.

Upon specifying the second magnetic sensing elements 112, the compensation signal generator 4 reads, from the memory, data (second output signals) output by the specified second magnetic sensing elements 112, among the digital signals subjected to the processing equivalent to low-pass filtering and stored in the memory. The data read by the compensation signal generator 4 indicates the magnetic properties detected by the magnetic sensing elements 11 positioned outside the sheet passage area, that is, magnetic noise depending on the surrounding environment. Then, the compensation signal generator 4 outputs the data indicating the magnetic noise depending on the surrounding environment read from the memory, to the environmental magnetism corrector 5.

Upon receiving the passage position information of the sheet 100 from the inspection device, the environmental magnetism corrector 5 specifies an area over which the sheet 100 passes in the magnetic sensor head 1, based on the passage position information. That is to say, the environmental magnetism corrector 5 specifies the sheet passage area. Then, the environmental magnetism corrector 5 specifies the first magnetic sensing elements 111 positioned inside the specified sheet passage area.

If the environmental magnetism corrector 5 specifies the first magnetic sensing elements 111, the environmental magnetism corrector 5 reads, from the memory, data (first output signals) output by the specified first magnetic sensing elements 111, among the digital signals stored in the memory. The data read by the environmental magnetism corrector 5 indicates the magnetic properties detected by the magnetic sensing elements 11 positioned inside the sheet passage area, that is, magnetic properties of the sheet 100 containing the magnetic noise depending on the surrounding environment. Then, the environmental magnetism corrector 5 subtracts the data indicating the magnetic noise depending on the surrounding environment, which was input or is to be input from the compensation signal generator 4, from the data indicating the magnetic properties of the sheet 100 read from the memory.

With the subtraction performed by the environmental magnetism corrector 5, the magnetic noise depending on the surrounding environment detected by the second magnetic sensing elements 112 can be removed from the magnetic properties of the sheet 100 containing the magnetic noise depending on the surrounding environment detected by the first magnetic sensing elements 111. Accordingly, the environmental magnetism corrector 5 can specify the magnetic properties of the sheet 100 only. The environmental magnetism corrector 5 outputs the subtraction result to the magnetic inspection determining processor 6.

Note that the compensation signal generator 4 specifies the second magnetic sensing elements 112 that are adjacent to the first magnetic sensing elements 111 respectively corresponding to one edge and the other edge of the sheet 100 in a direction that is orthogonal to the movement direction of the sheet 100. That is to say, the second magnetic sensing elements 112 positioned on both sides of the sheet passage area are specified. The compensation signal generator 4 performs moving average processing or average calculating processing on digital signals corresponding to the magnetic properties detected by the specified second magnetic sensing elements 112. Furthermore, the compensation signal generator 4 generates a compensation signal containing a magnetic noise gradient along the arrangement direction of the magnetic sensing elements 11 in the magnetic sensor head 1. Then, the environmental magnetism corrector 5 may perform subtraction using the compensation signal containing the magnetic noise gradient along the arrangement direction of the magnetic sensing elements 11 in the magnetic sensor head 1, generated by the compensation signal generator 4. That is to say, for example, the compensation signal generator 4 performs linear approximation on the generated compensation signal according to the distance in the direction of the magnetic sensor head 1. Then, the environmental magnetism corrector 5 may perform subtraction using the compensation signal according to the position of each magnetic sensing element 11.

Figure 9A:
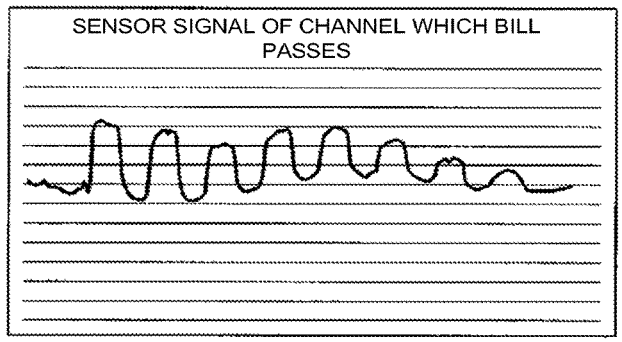
FIG. 9A is a chart showing an example of a digital signal in processing by a compensation signal generator and an environmental magnetism corrector.
Figure 9B:
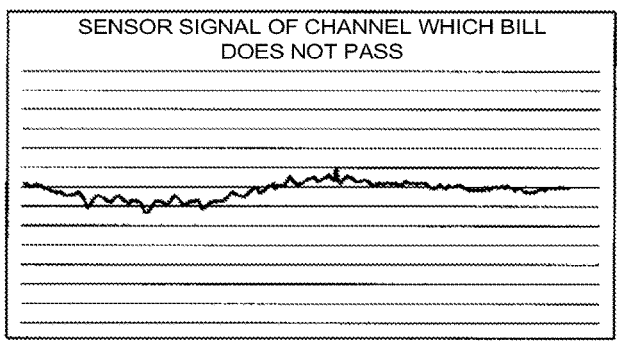
FIG. 9B is a chart showing an example of a digital signal in the processing by the compensation signal generator and the environmental magnetism corrector.
Figure 9C:
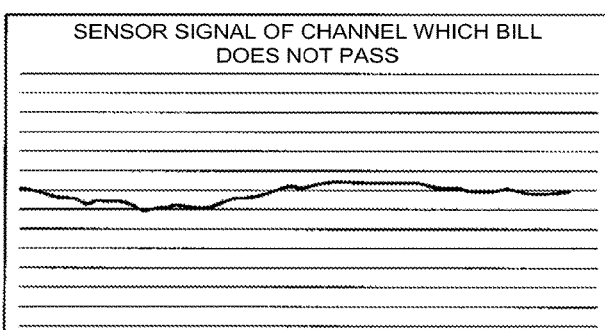
FIG. 9C is a chart showing an example of a digital signal in the processing by the compensation signal generator and the environmental magnetism corrector.
Figure 9D:
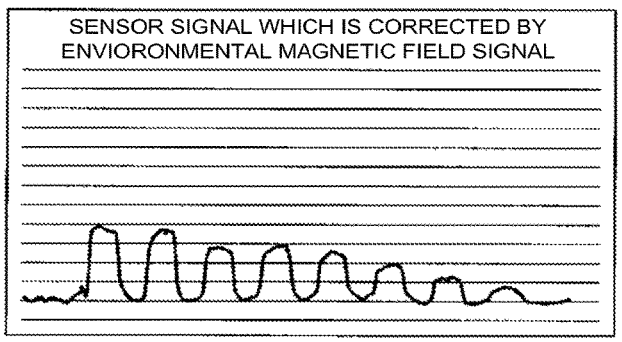
FIG. 9D is a chart showing an example of a digital signal in the processing by the compensation signal generator and the environmental magnetism corrector.

FIGS. 9A to 9D show charts of an example of a digital signal in the processing by the compensation signal generator 4 and the environmental magnetism corrector 5. FIG. 9A shows a digital signal indicating the magnetic properties of the sheet 100 containing the magnetic noise depending on the surrounding environment detected by the first magnetic sensing elements 111 specified by the environmental magnetism corrector 5. FIG. 9B shows a digital signal indicating the magnetic noise depending on the surrounding environment detected by the second magnetic sensing elements 112 specified by the compensation signal generator 4. FIG. 9C shows a digital signal after performing processing equivalent to low-pass filtering on the digital signal indicating the magnetic noise depending on the surrounding environment detected by the second magnetic sensing elements 112 specified by the compensation signal generating unit 4. FIG. 9D shows a signal obtained by subtracting the digital signal after performing the processing equivalent to low-pass filtering on the digital signal indicating the magnetic noise depending on the surrounding environment shown in FIG. 9C, from the digital signal indicating the magnetic properties of the sheet 100 containing the magnetic noise depending on the surrounding environment detected by the first magnetic sensing elements 111 shown in FIG. 9A. This digital signal indicates the magnetic properties of the sheet 100 only.

The description above relates to the processing performed by the magnetic detecting device 10. If the magnetic detecting device 10 performs this signal processing, it is possible to specify the magnetic properties of the sheet 100 only, obtained by removing the magnetic noise detected by the second magnetic sensing elements 112 from the signals detected by the first magnetic sensing elements 111 containing the magnetic noise depending on the surrounding environment.

Next, the magnetic inspection determining processor 6 receives input of the digital signals obtained by subtracting the digital signals indicating the magnetic noise from the digital signals from the first magnetic sensing element, from the environmental magnetism corrector 5. Then, the magnetic inspection determining processor 6 reads authenticity determination parameters stored in advance, from the determination reference level memory 7. The magnetic inspection determining processor 6 compares the digital signals input from the environmental magnetism corrector 5 with the read authenticity determination parameters, and, for example, obtains a square mean value. If the square mean value is within a predetermined range, the magnetic inspection determining processor 6 determines that the sheet 100 is genuine. If the square mean value is outside of the predetermined range, the magnetic inspection determining processor 6 determines that the sheet 100 is counterfeit.

The description above relates to the processing performed by the authenticity determining apparatus 30 including the magnetic detecting device 10 according to the first embodiment.

Note that the magnetic inspection determining processor 6 may perform determination using data corrected with a compensation signal containing a magnetic noise gradient along the arrangement direction of the magnetic sensing elements 11 in the magnetic sensor head 1, generated by the compensation signal generating unit 4. Furthermore, in the magnetic detecting device 10 according to the first embodiment, the second magnetic sensing elements 112 may be used as sensors for temperature correction used in known techniques.

As described above, in the magnetic detecting device 10 according to the first embodiment, the digital signal indicating the magnetic noise depending on the surrounding environment is subtracted from the digital signal indicating the magnetic properties of the sheet 100 containing the magnetic noise depending on the surrounding environment, based on the magnetism detection results (first output signals) detected by the first magnetic sensing elements 111 positioned inside the sheet passage area and the magnetism detection results (second output signals) detected by the second magnetic sensing elements 112 positioned outside the sheet passage area.

Thus, the magnetic detecting device 10 according to the first embodiment can specify the magnetic properties of the sheet 100 only, and can more precisely detect the magnetic properties of the sheet 100. Furthermore, the authenticity determining apparatus 30 including the magnetic detecting device 10 according to the first embodiment can compare the magnetic properties of the sheet 100 precisely detected by the magnetic detecting device 10 with the authenticity determination parameters, so that the level of precision in determining the authenticity can be increased.

Second Embodiment

The configuration of the magnetic detecting device 10 according to the second embodiment is similar to that in the first embodiment. Furthermore, the authenticity determining apparatus 30 including the magnetic detecting device 10 according to the second embodiment has a configuration similar to that in the first embodiment. Note that in the magnetic detecting device 10 according to the second embodiment, the magnetic sensor head 1 is magnetically shielded.

Figure 10A:
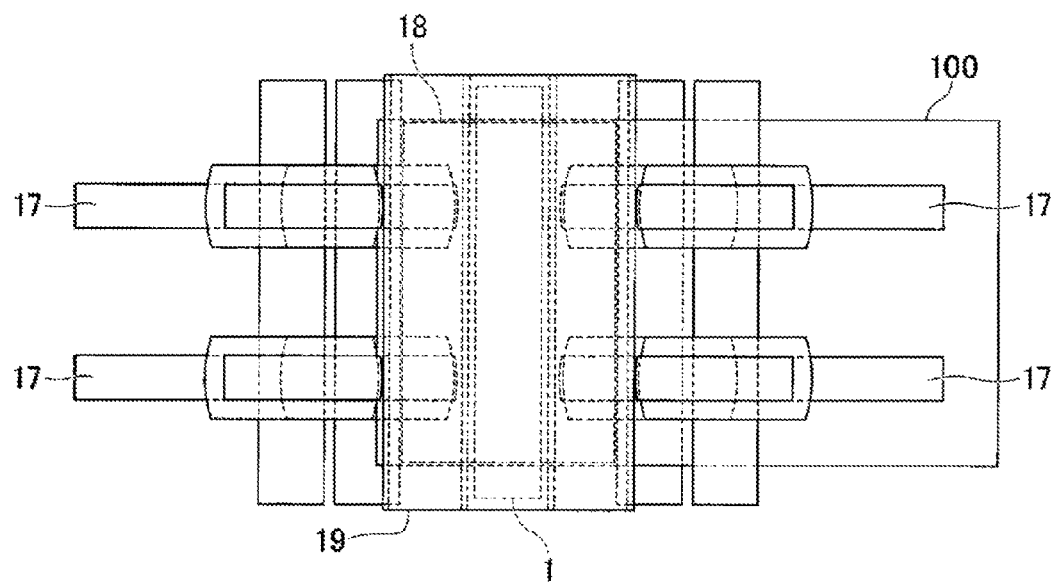
FIG. 10A is a view showing an example of a conveying structure around the magnetic sensor head of the magnetic detecting device according to a second embodiment.
Figure 10B:
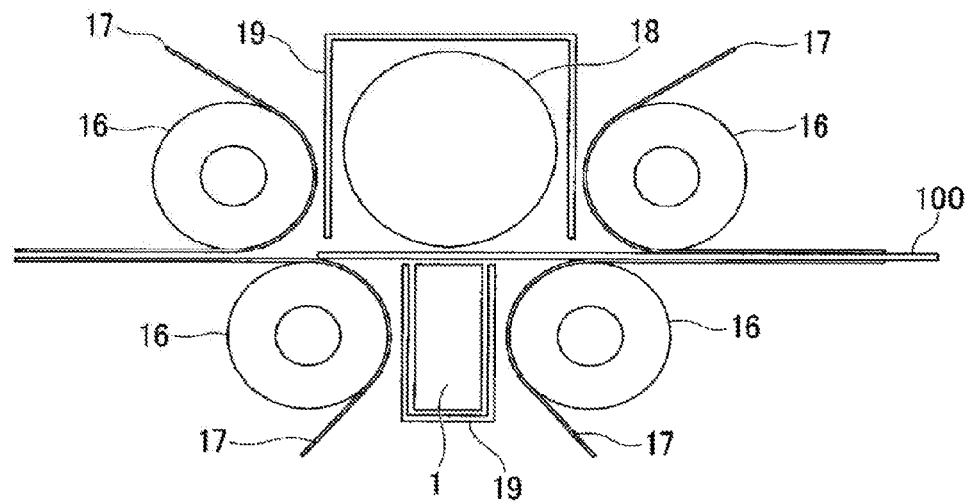
FIG. 10B is a view showing an example of the conveying structure around the magnetic sensor head of the magnetic detecting device according to the second embodiment.

FIG. 10A is a view showing an example of a conveying structure around the magnetic sensor head 1 of the magnetic detecting device 10 according to the second embodiment when viewed from above. FIG. 10B is a view showing an example of the conveying structure around the magnetic sensor head 1 of the magnetic detecting device 10 according to the second embodiment when viewed from a side.

As shown in FIGS. 10A and 10B, the magnetic detecting device 10 according to the second embodiment includes magnetic shield covers 19, which are magnetic shield structures made of a ferromagnetic material, in addition to the configuration of the magnetic detecting device 10 according to the first embodiment.

The magnetic shield covers 19 suppress the influence of a surrounding magnetic field environment when the magnetic sensing elements 11 of the magnetic sensor head 1 detect magnetic properties of the sheet 100. The magnetic shield cover 19 provided over the magnetic sensor head 1 has a structure in which a material having a high magnetic permeability such as iron encloses five faces (consisting of four sides and a rear face) of the magnetic sensing elements 11, but not the magnetic sensing face. Note that the magnetic sensing elements 11 are arranged such that each magnetic sensing face is oriented to an inspection target face of the sheet 100 that is being conveyed.

The magnetic shield cover 19 provided over the conveying assist roller 18 has a structure that encloses the conveying assist roller 18.

Accordingly, the magnetic shield covers 19 can suppress the influence of magnetic noise caused by rotationally driving bearings and transmitted from the rear face of the magnetic sensor head 1 and the like, on the magnetic property detection.

The magnetic shield covers 19 attract narrow magnetic fields (narrow ranges of magnetic field lines) of nearby magnetic field sources, into the shield material, thereby reducing the influence of the narrow ranges of magnetic field lines that enter the bias magnetic field area or the magnetic sensing faces of the magnetic sensing elements 11 in the magnetic sensor head 1 inside the magnetic shield covers 19. Furthermore, the magnetic shield covers 19 have an effect of increasing the uniformity in the magnetic field line distribution concentrated on the magnetic sensing elements 11 of the magnetic sensor head 1. Furthermore, the magnetic shield covers 19 have a function of reducing the influence of surrounding magnetic fields such that the magnetic fields uniformly affect the magnetic sensing elements 11 even in a surrounding magnetic field environment where a difference in the influences appears between the magnetic sensing elements 11.

Furthermore, the magnetic shield covers 19 can reduce the influence of nearby narrow magnetic fields on the magnetic property detection by the magnetic sensing elements 11, and can increase the uniformity in the influence. In a similar manner, the magnetic shield covers 19 can attenuate the influence of ferromagnetic fields of magnetic field sources such as motors and transformers inside the apparatus, on the magnetic property detection by the magnetic sensing elements 11, and increase the uniformity in the influence.

Accordingly, in the magnetic detecting device 10 according to the second embodiment further including the shield cover 19 in addition to the functional units of the magnetic detecting device 10 as in the first embodiment, the magnetic sensor head 1 is enclosed by the shield cover 19, so that the influence of narrow magnetic fields around the magnetic sensor head 1 on the magnetic property detection by the magnetic sensing elements 11 is attenuated and reduced. Furthermore, since the magnetic sensor head 1 is enclosed by the shield cover 19, the influence of wide and intense magnetic fields away from the magnetic sensor head 1 on the magnetic property detection by the magnetic sensing elements 11 is attenuated and reduced, so that the influence of environmental magnetic fields on the magnetic sensing elements 11 can be made uniform.

The magnetic detecting device 10 according to the second embodiment can have an increased level of precision in the detection by the magnetic sensing elements 11 of the magnetic sensor head 1, and can have an improved signal S/N ratio, which is the quality of obtained signals. Accordingly, the magnetic detecting device 10 can specify the magnetic properties of the sheet 100 only, and can more precisely detect the magnetic properties of the sheet 100.

Furthermore, the authenticity determining apparatus 30 including the magnetic detecting device 10 according to the second embodiment can compare the more precise magnetic properties with the authenticity determination parameters, based on the magnetic properties of the sheet 100 more precisely detected by the magnetic detecting device 10, so that the level of precision in determining the authenticity can be increased.

Third Embodiment

Figure 11:
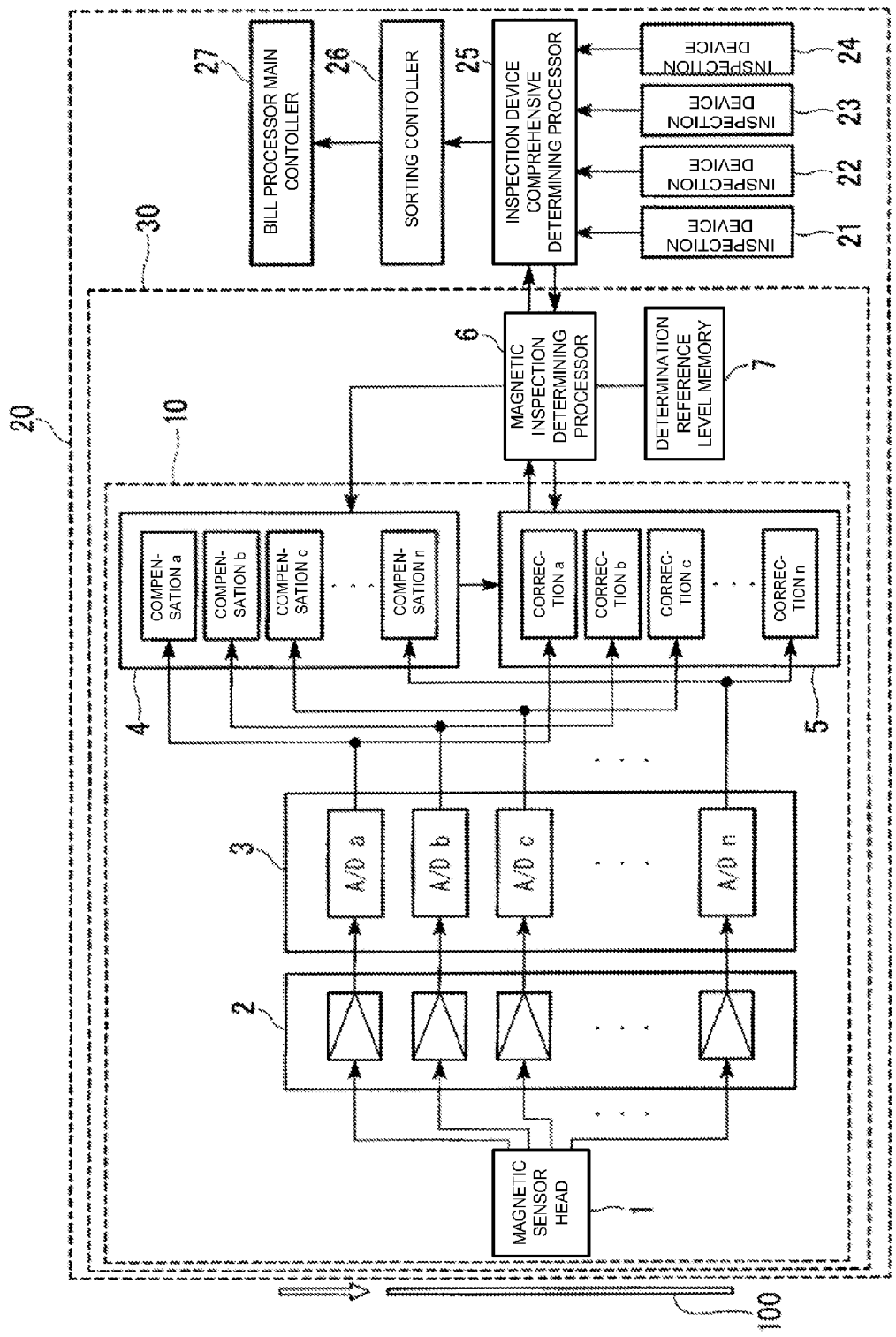
FIG. 11 is a diagram showing the configuration of a sheet processing apparatus according to the third embodiment.

FIG. 11 is a diagram showing the configuration of a sheet processing apparatus 20 according to the third embodiment.

In the third embodiment, bills are used as the sheet 100. The sheet processing apparatus 20 according to the third embodiment includes the authenticity determining apparatus 30 including the magnetic detecting device 10 according to the first embodiment, inspection devices 21 to 24, an inspection device comprehensive determining processor 25, a sorting controller 26, and a bill processor main controller 27. The authenticity determining apparatus 30 includes the magnetic sensor head 1, the signal amplifier circuit 2, the A/D converter circuit 3, the compensation signal generating unit 4, the environmental magnetism corrector 5, the magnetic inspection determining processor 6, and the determination reference level memory 7.

In this example, the inspection devices 21 to 24 included in the sheet processing apparatus 20 according to the third embodiment perform inspection for sorting the sheets 100 into sheets that are genuine, to be discarded, to be re-circulated, or to be eliminated, according to the state of the sheet 100. For example, the inspection devices 21 to 24 may be a ripping detecting device for detecting ripping of the sheet 100, a thickness inspection device for inspecting the thickness of the sheet 100, a shape and watermark detecting device for detecting the shape and the watermark of the sheet 100, an optical pattern determining device for determining the optical pattern of the sheet 100, or the like.

The inspection device comprehensive determining processor 25 is a processor for specifying the authenticity of the sheet 100 and the deterioration level of the sheet 100 based on the inspection results of the inspection devices 21 to 24 and the magnetic detecting device 10. Furthermore, the inspection device comprehensive determining processor 25 is a processor for controlling the conveyance of the sheet 100 in the inspection devices 21 to 24 and the magnetic detecting device 10. With the control performed by the inspection device comprehensive determining processor 25, the magnetic detecting device 10 can specify the position over which the sheet 100 passes in the magnetic sensor head 1. If the control by the inspection device comprehensive determining processor 25 is precise, the magnetic detecting device 10 can specify the first magnetic sensing elements 111 and the second magnetic sensing elements 112 in advance.

The sorting controller 26 is a processor for sorting the sheets 100 into sheets that are to be discarded, to be re-circulated, or to be eliminated, based on the authenticity of the sheets 100 and the deterioration level of the sheets 100 specified by the inspection device comprehensive determining processor 25.

The bill processor main controller 27 performs discarding, re-circulating, or eliminating processing according to the sorting by the sorting controller 26.

Hereinafter, an example of processing by the sheet processing apparatus 20 according to the third embodiment will be described.

First, a user sets the sheet 100 at a predetermined position. Subsequently, when the sheet processing apparatus 20 is started, the sheet 100 is taken out sheet by sheet and conveyed, so that each sheet 100 passes through the inspection device 21, the inspection device 22, the inspection device 23, the magnetic detecting device 10, and the inspection device 24 in this order, and each of the devices 21, 22, 23, 10, and 24 performs the inspection processing on the sheet 100.

The inspection device 21 performs inspection of whether or not there is ripping of the sheet 100. The inspection device 21 includes, for example, a structure such as a roller, on the conveying route on which the sheet 100 is conveyed, and this structure opens a rip if it is present at an edge of the sheet 100. The inspection device 21 performs inspection of whether or not there is a rip based on whether or not there is light that passes through the opened rip. The rip inspection is performed for detecting sheets 100 that are not suitable for re-circulation. If a rip is detected in the sheet 100, the inspection device 21 notifies the inspection device comprehensive determining processor 25 of that a rip has been detected.

The inspection device 22 performs inspection of the thickness of the sheet 100. The inspection device 22 includes, for example, a structure for detecting the thickness of the sheet 100 such as a thickness sensor, on the conveying route on which the sheet 100 is conveyed. The inspection device 22 determines whether or not the detected thickness is within a predetermined thickness range. In this inspection, if the thickness of the sheet 100 is a predetermined thickness or more, it is determined that two or more sheets are overlapping, and the inspection device 22 notifies the inspection device comprehensive determining processor 25 of the result.

The inspection device 23 performs inspection of the shape and the watermark of the sheet 100. The inspection device 23 includes, for example, a structure for detecting the characteristics of a transmission image of the sheet 100, on the conveying route on which the sheet 100 is conveyed. The inspection device 23 compares the detected characteristics with the characteristics of a genuine bill, and notifies the inspection device comprehensive determining processor 25 of the result.

The inspection device 24 performs inspection of an optical pattern. The inspection device 24 includes, for example, a structure for detecting the characteristics of a reflected light image of the sheet 100, on the conveying route on which the sheet 100 is conveyed. The inspection device 24 compares the detected characteristics with the characteristics of a genuine bill, and notifies the inspection device comprehensive determining processor 25 of the result.

The magnetic detecting device 10 detects magnetic properties of the sheet 100, thereby inspecting the authenticity of the sheet 100. The authenticity determination performed by the authenticity determining apparatus 30 including the magnetic detecting device 10 is, for example, the authenticity determination by the processing described in the first embodiment. Thus, a detailed description thereof has been omitted. The authenticity determining apparatus 30 notifies the inspection device comprehensive determining processor 25 of the result determined by the authenticity determining apparatus 30.

The inspection device comprehensive determining processor 25 comprehensively determines whether the sheet 100 that is being conveyed is genuine, to be discarded, to be re-circulated, or to be eliminated, based on the results notified from the inspection devices 21 to 24 and the authenticity determining apparatus 30. The inspection device comprehensive determining processor 25 notifies the sorting controller 26 of this determination result.

The sorting controller 26 determines where the sheet 100 is to be sorted, based on the notified information.

As described above, the sheet processing apparatus 20 according to the third embodiment performs inspection using the authenticity determining apparatus 30 including the magnetic detecting device 10 according to the first embodiment, as one type of inspection for determining whether the sheet 100 is to be discarded, to be re-circulated, or to be eliminated.

The magnetic detecting device 10 of the sheet processing apparatus 20 according to the third embodiment can precisely detect the magnetism of the sheet 100. Thus, the sheet processing apparatus 20 including the authenticity determining apparatus 30 including the magnetic detecting device 10 according to the third embodiment can compare the precise magnetic properties with the authenticity determination parameters, based on the precisely detected magnetic properties of the sheet 100, so that the level of precision in determining the authenticity can be increased.

Note that the sheet processing apparatus 20 is not limited to an apparatus for determining whether the sheet 100 is to be discarded, to be re-circulated, or to be eliminated in this manner, and may be any apparatus as long as it can at least determine the authenticity of the sheet 100 based on information on the magnetism of the sheet 100 and sort the sheet 100.

In the magnetic detecting device 10 according to at least one of the foregoing embodiments, a digital signal indicating the magnetic noise depending on the surrounding environment is subtracted from a digital signal indicating the magnetic properties of the sheet 100 containing the magnetic noise depending on the surrounding environment, based on magnetism detection results (first output signals) detected by the first magnetic sensing elements 111 positioned inside the sheet passage area in the magnetic sensor head 1 and magnetism detection results (second output signals) detected by the second magnetic sensing elements 112 positioned outside the sheet passage area in the magnetic sensor head 1.

Thus, the magnetic detecting device 10 according to the first embodiment can specify the magnetic properties of the sheet 100 only, and can more precisely detect the magnetic properties of the sheet 100. Furthermore, the sheet processing apparatus 20 including the authenticity determining apparatus 30 including the magnetic detecting device 10 according to the first embodiment can compare the more precise magnetic properties with the authenticity determination parameters, based on the magnetic properties of the sheet 100 more precisely detected by the magnetic detecting device 10, so that the level of precision in determining the authenticity can be increased.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic detecting device, comprising:
a magnetic sensor head having a plurality of magnetic sensing elements including a first magnetic sensing element and a second magnetic sensing element arranged in one line over a length that is greater than a width of a sheet in a direction that is orthogonal to a movement direction of the sheet; and
an environmental magnetism corrector configured to correct a first output signal output by the first magnetic sensing element based on a second output signal output by the second magnetic sensing element, wherein
the magnetic sensor head has a sheet passage area that faces a sheet that passes over the magnetic sensor head,
the first magnetic sensing element is positioned inside the sheet passage area, and
the second magnetic sensing element is positioned outside the sheet passage area.

2. The magnetic detecting device according to claim 1, wherein the environmental magnetism corrector is configured to correct the first output signal based on a magnetic noise gradient obtained by performing linear approximation on the second output signal based on the second output signal output by the second magnetic sensing element positioned on both sides of the sheet passage area.

3. The magnetic detecting device according to claim 1, wherein the environmental magnetism corrector is configured to specify the first magnetic sensing element based on a passage position of the sheet.

4. The magnetic detecting device according to claim 1, further comprising:
a roller configured to restrict a distance between the sheet that passes over the magnetic sensor head and the magnetic sensor head to within a predetermined range, the roller being disposed so as to face the magnetic sensor head; and
magnetic shield covers configured to enclose the magnetic sensor head and the roller.

5. The magnetic detecting device according to claim 1, wherein magnetic sensing faces of the plurality of magnetic sensing elements are formed on the same plane and along one straight line.

6. The magnetic detecting device according to claim 2, further comprising a magnetic shield cover configured to enclose the magnetic sensor head.

7. The magnetic detecting device according to claim 5, further comprising a compensation signal generator configured to
perform processing that removes a sudden change with respect to a time axis direction from the second output signal output by the second magnetic sensing element, and
output a result of the processing.

8. The magnetic detecting device according to claim 7, wherein
the second output signal is sampled in the time axis direction, and
the compensation signal generator is configured to perform moving average processing that averages a plurality of signals sampled.

9. The magnetic detecting device according to claim 1, wherein the environmental magnetism corrector is configured to correct the first output signal based on a processing result obtained by performing processing that removes a sudden change with respect to a time axis direction from the second output signal.

10. The magnetic detecting device according to claim 9, wherein the processing that removes a sudden change with respect to the time axis direction from the second output signal is processing that samples the second output signal in the time axis direction and averages a plurality of signals sampled.

11. A magnetic detecting device, comprising:
a magnetic sensor head having a sheet passage area that faces a sheet that passes over the magnetic sensor head, wherein a plurality of magnetic sensing elements are arranged in one line over a length that is greater than a width of the sheet in a direction that is orthogonal to a movement direction of the sheet; and
an environmental magnetism corrector configured to correct a first output signal output by one of the plurality of magnetic sensing elements positioned inside the sheet passage area based on a second output signal output by another of the plurality magnetic sensing elements positioned outside the sheet passage area.

* * * * *